H US011207285B2

United States Patent
Bar-Tana

(10) Patent No.: US 11,207,285 B2
(45) Date of Patent: Dec. 28, 2021

(54) DIABETES TREATMENT REGIMENS USING ALPHA, ALPHA-SUBSTITUTED LONG-CHAIN AMPHIPATHIC CARBOXYLATES

(71) Applicant: SYNDROMEX LTD., Jerusalem (IL)

(72) Inventor: Jacob Bar-Tana, Jerusalem (IL)

(73) Assignee: SYNDROMEX LTD., Jerusalem (IL)

( * ) Notice: Subject to any disclaimer, the term of this patent is extended or adjusted under 35 U.S.C. 154(b) by 318 days.

(21) Appl. No.: 16/305,700

(22) PCT Filed: May 29, 2017

(86) PCT No.: PCT/IL2017/050596
§ 371 (c)(1),
(2) Date: Nov. 29, 2018

(87) PCT Pub. No.: WO2017/208232
PCT Pub. Date: Dec. 7, 2017

(65) Prior Publication Data
US 2020/0375933 A1 Dec. 3, 2020

Related U.S. Application Data

(60) Provisional application No. 62/344,480, filed on Jun. 2, 2016.

(51) Int. Cl.
*A61K 31/20* (2006.01)
*A61P 3/10* (2006.01)
*A61K 31/155* (2006.01)

(52) U.S. Cl.
CPC ............ *A61K 31/20* (2013.01); *A61K 31/155* (2013.01); *A61P 3/10* (2018.01)

(58) Field of Classification Search
CPC .......... A61K 31/20; A61K 31/155; A61P 3/10
See application file for complete search history.

(56) References Cited

U.S. PATENT DOCUMENTS

2013/0303446 A1  11/2013  Hamilton et al.

FOREIGN PATENT DOCUMENTS

| WO | 98/30530 A1 | 7/1998 |
|---|---|---|
| WO | 2004/056740 A1 | 7/2004 |
| WO | 2005002557 A1 | 1/2005 |
| WO | 2008104975 A2 | 9/2008 |
| WO | WO 2008/104975 | * 9/2008 |

OTHER PUBLICATIONS

Park, KS. "Prevention of type 2 diabetes mellitus from the viewpoint of genetics." Diabetes Research and Clinical Practice. 2004; 66S: S33-S35.*
Graham et al. Clinical pharmacokinetics of metformin. (Clin. Pharmacokinet. 2011; 50(2): 81-98).*
Dorwald (Side Reactions in Organic Synthesis: A Guide to Successful Synthesis Design, Weinheim: WILEY-VCH Verlag GmbH & Co. KGaA, 2005, Preface).*
Umegaki H., "Chapter 19 Neurodegeneration in Diabetes Mellitus", Adv. Exp. Med. Biol. 2012; 724:258-65.
Onitilo, AA et al., "Diabetes and cancer I: risk, survival, and implications for screening", Cancer Causes Control, 2012 23(6):967-81.
Deng, L. et al, "Diabetes Mellitus and the Incidence of Colorectal Cancer: An Updated Systematic Review and Meta-Analysis", Dig. Dis. Sci. 2012 57(6):1576-85.
Liao, S. et al., Association between Diabetes Mellitus and Breast Cancer Risk: a Meta-analysis of the Literature:, Asian Pac. J. Cancer Prev. 2011 12(4):1061-5.
Janghorbani, M. et al., "Systematic Review and Meta-analysis of Insulin Therapy and Risk of Cancer", Horm. Cancer, 2012 3(4):137-46.
Cheung BM, "Diabetes Prevalence and Therapeutic Target Achievement in the United States, 1999 to 2006", The American Journal of Medicine, 122:443-53 (2009).
Hirst JA, et al., "Changes in HbA1c Level over a 12-Week Follow-up in Patients with Type 2 Diabetes following a Medication Change", PLoS One. 25:9: e92458 (2014).
Beltran Del Rio M, "Glycated Hemoglobin, Plasma Glucose, and Erythrocyte Aging". Journal of Diabetes Science & Technology 10:1303-1307 (2016).
Zatara, "Suppression of FoxOI Activity by Long-Chain Fatty Acyl Analogs", Diabetes, vol. 60, 2011.
Kalderon, "Suppression of adipose lipolysis by long-chain fatty acid analogs", Journal of Lipid Research vol. 53, 2012.
Zatara et al., AMPK activation by long chain fatty acyl analogs, Biochemical Pharmacology vol. 76, No. 10, pp. 1263-1275, 2008.
Tahrani et al., Glycaemic control in type 2 diabetes: Targets and new therapies, Pharmacology & Therapeuties 125, 328-361, 2010.
Shannon Reagan-Shaw et al., Dose translation from animal to human studies revisited, The FASEB Journal, vol. 22, No. 3, pp. 659-661, 2008.

* cited by examiner

*Primary Examiner* — Theodore R. Howell
(74) *Attorney, Agent, or Firm* — Browdy and Neimark, PLLC

(57) ABSTRACT

Disclosed are methods of treating of type 2 diabetes mellitus and associated conditions in humans by administering an α,α-substituted long-chain dicarboxylic acid. In some of the disclosed methods the α,α-substituted long-chain dicarboxylic acid is administered as add-on therapy to anti-diabetic Standard-of-Care treatment.

16 Claims, No Drawings

DIABETES TREATMENT REGIMENS USING ALPHA, ALPHA-SUBSTITUTED LONG-CHAIN AMPHIPATHIC CARBOXYLATES

FIELD OF THE INVENTION

The present invention relates to regimens and methods for the treatment of diabetes in patients suffering from diabetes mellitus type 2 or pre-diabetes type 2, using α,α-substituted long-chain amphipathic carboxylates.

BACKGROUND OF THE INVENTION

Type 2 Type 2 diabetes mellitus (T2D) is generally, although not always, associated with a group of metabolic pathologies/symptoms/diseases in one person, including abdominal obesity (excessive fat tissue in the abdomen); dyslipidemia (blood lipid disorders—high triglycerides, low HDL-cholesterol and/or high small-dense LDL-cholesterol—that foster plaque buildups in artery walls); elevated blood pressure; prothrombotic state (e.g., high fibrinogen or plasminogen activator inhibitor-1 in blood); and proinflammatory state (e.g., elevated C-reactive protein in blood). Patients with T2D are at increased risk of macrovascular diseases (diseases related to atherosclerotic plaque buildups in artery walls (e.g., coronary heart disease, cerebrovascular and peripheral vascular disease), microvascular diseases (e.g., retinopathy, nephropathy neuropathy), cancer (e.g., pancreatic, breast, colorectal, other) and neurodegeneration (e.g., dementia, Alzheimer). Prediabetic subjects are at high risk of developing T2D.

T2D is a metabolic disorder characterized by chronic hyperglycemia with disturbances of carbohydrate, fat and protein metabolism resulting from defects in insulin secretion, insulin action, or both. The effects of T2D include long-term damage, dysfunction and failure of various organs. In its most severe forms, ketoacidosis or a non-ketotic hyperosmolar state may develop and lead to stupor, coma and, in absence of effective treatment, death. Often, symptoms are not severe or may be absent, and consequently mild hyperglycaemia and/or hyperinsulinemia and/or dyslipidemia sufficient to cause pathological and functional changes may be present for a long time before diagnosis is made. The long-term effects of T2D include progressive development of the specific complications of retinopathy with potential blindness, and/or nephropathy, that may lead to renal failure, and/or neuropathy with risk of foot ulcers, leg amputation, Charcot joints, and features of autonomic dysfunction, including sexual dysfunction. People with diabetes are at increased risk of cardiovascular, peripheral vascular and cerebrovascular disease.

Recent studies revealed that T2D is a risk factor for cognitive dysfunction or dementia, especially those related to Alzheimer's disease (AD). Insulin resistance, often associated with T2D, may induce a deficiency of insulin effects in the central nervous system (CNS). Insulin may have a neuroprotective role and may have some impact on acetylcholine (ACh) synthesis. Hyperinsulinemia, induced by insulin resistance occurring in T2D, may be associated with insulin deficiency caused by reduced insulin transport via the blood brain barrier (BBB). Insulin has multiple important functions in the brain. Some basic research, however, suggests that hyperinsulinemia and/or insulin resistance accelerate Alzheimer-related pathology through effects on the amyloid beta (Aβ) metabolism and tau proteins phosphorylation (Umegaki H., Adv. Exp. Med. Biol. 2012; 724:258-65).

T2D and cancer are common diseases that are frequently diagnosed in the same individual, and an association between the two conditions has long been postulated. Epidemiological evidence for increased risk of cancer, and decreased cancer survival in diabetic patients has been shown (Onitilo, A A et al., Cancer Causes Control, 201223 (6):967-81). These authors have shown that the risk for several cancers, including cancers of the pancreas, liver, colorectal, breast, urinary tract, and endometrium, is increased in patients with diabetes mellitus. T2D also impacts negatively on cancer-related survival outcomes. The overwhelming evidence for increased incidence of certain cancers, and poorer prognosis after cancer diagnosis in diabetic patients dictates a need for improved cancer care in diabetic individuals through improved screening measures, development of risk assessment tools, and consideration of cancer prevention strategies in diabetic patients. Another study supported a relationship between diabetes and increased risk of colon and rectal cancer in both women and men, and that insulin therapy for diabetes may increase this risk (Deng, L. et al, Dig. Dis. Sci. 201257(6):1576-85). A further meta-analysis study indicated that T2D can be considered as a risk factor for breast cancer (Liao, S. et al. Asian Pac. J. Cancer Prev. 2011 12(4):1061-5). Some epidemiological studies suggested that treatment with insulin may promote cancer growth. A systematic review and meta-analysis of published observational studies conducted to assess the risk of cancer during treatment with insulin concluded that insulin treatment was associated with an increased risk of overall, pancreatic and colorectal cancer (Janghorbani, M. et al., Horm. Cancer, 20123(4):137-46).

In contrast to insulin, insulin sensitizers used in the treatment of T2D, predominantly metformin, have proved efficient for treating cancer types associated with T2D.

Amphipathic long chain α,α-disubstituted dicarboxylic acids (also referred to as αα-Medica drugs) are described in WO1998/030530. Some specific compounds disclosed in this publication are 2,2,15,15-tetramethyl-hexadecane-1,16-dioic acid (also referred to herein as Medica16αα or M16αα) and 2,2,17,17-tetramethylocta-decane-1,18-dioic acid (also referred to herein as Medica18αα or M18αα).

T2D and its related symptoms, as well as other pathologies associated with the Metabolic Syndrome, are to be treated chronically. Search has been made for novel drugs and novel treatment regimens, which can significantly improve or replace current treatment protocols.

SUMMARY

In a first aspect, disclosed herein is a method of treating type 2 diabetes mellitus in a human subject in need thereof, wherein said human subject receives ongoing standard-of-care treatment with at least one anti-diabetic drug, said method comprising administering to said human subject a therapeutically effective amount of an amphipathic α,α-substituted long-chain dicarboxylic acid of the formula (I):

$$HOOC-CR_1R_2-Q-CR_3R_4-COOH \qquad (I)$$

wherein $R_1$, $R_2$, $R_3$ and $R_4$, each independently represents an optionally substituted alkyl, alkenyl, alkynyl, cycloalkyl, aryl, aralkyl or a lower alkoxy group; and Q represents a diradical consisting of a linear chain of 12 to 16 carbon atoms, one or more of which may be optionally be replaced by heteroatoms selected from N, P, O and S, said chain being optionally substituted by inert substituents, and wherein optionally one or more of said carbon or heteroatom chain members forms part of a ring structure, and pharmaceutically acceptable salt, ester, amide, anhydride or lactone thereof, specifically a salt, ester or amide thereof. In some specific embodiments administration is oral.

In a second aspect, disclosed herein is a method of treating and/or preventing a pathology, symptom and/or disease associated with type 2 diabetes mellitus in a human subject in need thereof, wherein said human subject receives ongoing standard-of-care treatment with at least one anti-diabetic drug, said method comprising administering to said human subject a therapeutically effective amount of an amphipathic α,α-substituted long-chain dicarboxylic acid of the formula (I):

HOOC—CR$_1$R$_2$-Q-CR$_3$R$_4$—COOH   (I)

wherein

R$_1$, R$_2$, R$_3$ and R$_4$, each independently represents an optionally substituted alkyl, alkenyl, alkynyl, cycloalkyl, aryl, aralkyl or a lower alkoxy group; and Q represents a diradical consisting of a linear chain of 12 to 16 carbon atoms, one or more of which may be optionally be replaced by heteroatoms selected from N, P, O and S, said chain being optionally substituted by inert substituents, and wherein optionally one or more of said carbon or heteroatom chain members forms part of a ring structure, and pharmaceutically acceptable salt, ester, amide, anhydride or lactone thereof, specifically a salt, ester or amide thereof. In some specific embodiments administration is oral.

In a third aspect, disclosed herein is a method for maintaining or reducing standard-of-care administered dose of an anti-diabetic drug, or for obviating the need for administration of such drug in a type 2 diabetes mellitus subject in need thereof, said method comprising administering to said human subject a therapeutically effective amount of an amphipathic α,α-substituted long-chain dicarboxylic acid of the formula (I):

HOOC—CR$_1$R$_2$-Q-CR$_3$R$_4$—COOH   (I)

wherein

R$_1$, R$_2$, R$_3$ and R$_4$, each independently represents an optionally substituted alkyl, alkenyl, alkynyl, cycloalkyl, aryl, aralkyl or a lower alkoxy group; and Q represents a diradical consisting of a linear chain of 12 to 16 carbon atoms, one or more of which may be optionally be replaced by heteroatoms selected from N, P, O and S, said chain being optionally substituted by inert substituents, and wherein optionally one or more of said carbon or heteroatom chain members forms part of a ring structure, and pharmaceutically acceptable salt, ester, amide, anhydride or lactone thereof, specifically a salt, ester or amide thereof. In some specific embodiments administration is oral.

In said methods of the first, second and third aspects of the present disclosure, said ongoing standard-of-care treatment comprises administration of at least one topical, oral or parenteral anti-diabetic drug. The orally administered anti-diabetic drug can be any one of metformin, glitazones, sulphonylureas, meglitinides, acarbose, DPP4 inhibitors or SGLT2 inhibitors, or any mixtures of at least two thereof. The parenterally administered anti-diabetic drug can be any one of GLP1 analogs, insulin or insulin analogs, or any mixtures of at least two thereof.

In said methods of the first, second and third aspects of the present disclosure, the said pathology, symptom or disease associated with type 2 diabetes mellitus can be any one of insulin resistance, hyperglycemia, obesity/overweight, diabetic dyslipidemia, diabetic hypertriglyceridemia, diabetes-associated neurodegeneration, diabetes macrovascular disease, or diabetes microvascular disease, or any combination thereof.

In said methods of the first, second and third aspects of the present disclosure, the said therapeutically effective amount of said α,α-substituted long-chain dicarboxylic acid or pharmaceutically acceptable salt, ester, amide, anhydride or lactone thereof administered to said human subject is from about 10 mg per day to about 200 mg per day, 10 mg per day to about 150 mg per day, 10 mg per day to about 100 mg per day, or 10 mg per day to about 50 mg per day. The said amphipathic dicarboxylic acid of Formula (I) can be administered to said subject once or twice daily, or once, twice or three times weekly. In other embodiments, said amphipathic dicarboxylic acid of Formula (I) can be administered chronically. In some specific embodiments administration is oral.

In said methods of the first, second and third aspects of the present disclosure, insulin resistance of said subject is decreased compared to the insulin resistance of said subject before/without treatment with said α,α-substituted long-chain dicarboxylic acid or pharmaceutically acceptable salt, ester, amide, anhydride or lactone thereof; and/or the level of fasting plasma/blood glucose of said subject is decreased compared to the fasting plasma/blood glucose of said subject before/without treatment with said α,α-substituted long-chain dicarboxylic acid or pharmaceutically acceptable salt, ester, amide, anhydride or lactone thereof; and/or the blood level of glycosylated hemoglobin A1$_C$ of said subject is decreased compared to the level of glycosylated hemoglobin A1$_C$ of said subject before/without treatment with said α,α-substituted long-chain dicarboxylic acid or pharmaceutically acceptable salt, ester, amide, anhydride or lactone thereof; and/or glucose tolerance of said subject is increased compared to the glucose tolerance of said subject before/without treatment with said α,α-substituted long-chain dicarboxylic acid or pharmaceutically acceptable salt, ester, amide, anhydride or lactone thereof.

In a fourth aspect, disclosed herein is a method of preventing and/or delaying the onset of type 2 diabetes mellitus or the onset of anti-diabetic treatment in a pre-type 2 diabetic human subject, or in an impaired-glucose tolerance (IGT) human subject, or in an impaired fasting glucose (IFG) human subject, wherein said human subject receives anti-diabetic standard-of-care treatment, said method comprising administering to said human subject a therapeutically effective amount of an of an amphipathic α,α-substituted long-chain dicarboxylic acid of the formula (I):

HOOC—CR$_1$R$_2$-Q-CR$_3$R$_4$—COOH   (I)

wherein

R$_1$, R$_2$, R$_3$ and R$_4$, each independently represents an optionally substituted alkyl, alkenyl, alkynyl, cycloalkyl, aryl, aralkyl or a lower alkoxy group; and Q represents a diradical consisting of a linear chain of 12 to 16 carbon atoms, one or more of which may be optionally be replaced by heteroatoms selected from N, P, O and S, said chain being optionally substituted by inert substituents, and wherein optionally one or more of said carbon or heteroatom chain members forms part of a ring structure, and pharmaceutically acceptable salt, ester, amide, anhydride or lactone thereof, specifically salt, ester or amide thereof. In some specific embodiments administration is oral.

In a fifth aspect, disclosed herein is a method of decreasing insulin resistance, and/or fasting blood glucose level, and/or level of glycosylated hemoglobin A1$_C$, and/or

increasing glucose tolerance in pre-type 2 diabetic or hyperglycemic type 2 diabetes mellitus human subject, wherein said human subject receives anti-diabetic standard-of-care treatment, said method comprising in some specific embodiments administering to said human subject a therapeutically effective amount of an amphipathic α,α-substituted long-chain dicarboxylic acid of the formula (I):

HOOC—CR$_1$R$_2$-Q-CR$_3$R$_4$—COOH     (I)

wherein

R$_1$, R$_2$, R$_3$ and R$_4$, each independently represents an optionally substituted alkyl, alkenyl, alkynyl, cycloalkyl, aryl, aralkyl or a lower alkoxy group; and Q represents a diradical consisting of a linear chain of 12 to 16 carbon atoms, one or more of which may be optionally be replaced by heteroatoms selected from N, P, O and S, said chain being optionally substituted by inert substituents, and wherein optionally one or more of said carbon or heteroatom chain members forms part of a ring structure, and pharmaceutically acceptable salt, ester, amide, anhydride or lactone thereof, specifically salt, ester or amide thereof. In some specific embodiments administration is oral.

In said fourth and fifth aspects of the present disclosure, said standard-of-care treatment comprises (1) Therapeutic Lifestyle Change (TLC) including dietary measures and/or physical exercise and/or (2) topical, oral or parenteral administration to said subject of said at least one standard-of-care anti-diabetic drug. The said orally administered standard-of-care anti-diabetic drug can be any of metformin, glitazones, sulphonylureas, meglitinides, acarbose, DPP4 inhibitors or SGLT2 inhibitors, or any mixture of at least two thereof. The said parenterally administered standard-of-care anti-diabetic drug can be any one of GLP1 analogs, insulin or insulin analogs, or a mixture of at least two thereof.

In said fourth and fifth aspects of the present disclosure, insulin resistance of said subject is decreased compared to the insulin resistance of said subject before/without treatment with said amphipathic α,α-substituted long-chain dicarboxylic acid or pharmaceutically acceptable salt, ester, amide anhydride or lactone thereof, specifically salt, ester or amide thereof; and/or the plasma/blood level of fasting glucose of said subject is decreased compared to the fasting plasma/blood glucose of said subject before/without treatment with said amphipathic α,α-substituted long-chain dicarboxylic acid or pharmaceutically acceptable salt, ester, amide anhydride or lactone thereof, specifically salt, ester or amide thereof; and/or the blood level of glycosylated hemoglobin A1$_C$ of said subject is decreased compared to the level of glycosylated hemoglobin A1$_C$ of said subject before/without treatment with said amphipathic α,α-substituted long-chain dicarboxylic acid or pharmaceutically acceptable salt, ester, amide anhydride or lactone thereof, specifically salt, ester or amide thereof; and/or glucose tolerance of said subject is improved compared to the glucose tolerance of said subject before/without treatment with said amphipathic α,α-substituted long-chain dicarboxylic acid or pharmaceutically acceptable salt, ester, amide anhydride or lactone thereof, specifically salt, ester or amide thereof.

In said fourth and fifth aspects of the present disclosure, said therapeutically effective amount of said amphipathic α,α-substituted long-chain dicarboxylic acid or pharmaceutically acceptable salt, ester, amide, anhydride or lactone thereof is from about 10 mg per day to about 200 mg per day, 10 mg per day to about 150 mg per day, 10 mg per day to about 100 mg per day, or 10 mg per day to about 50 mg per day. The said amphipathic α,α-substituted long-chain dicarboxylic acid or pharmaceutically acceptable salt, ester, amide, anhydride or lactone thereof can be administered once or twice daily, or once, twice or three times weekly. The said amphipathic α,α-substituted long-chain dicarboxylic acid or pharmaceutically acceptable salt, ester, amide, anhydride or lactone thereof can be administered chronically. In some specific embodiments administration is oral.

In yet a further, sixth aspect, disclosed herein is a method of treating type 2 diabetes mellitus in a human subject in need thereof, comprising administering to said human subject a therapeutically effective amount of an amphipathic α,α-substituted long-chain dicarboxylic acid of the formula (I):

HOOC—CR$_1$R$_2$-Q-CR$_3$R$_4$—COOH     (I)

wherein

R$_1$, R$_2$, R$_3$ and R$_4$, each independently represents an optionally substituted alkyl, alkenyl, alkynyl, cycloalkyl, aryl, aralkyl or a lower alkoxy group; and Q represents a diradical consisting of a linear chain of 12 to 16 carbon atoms, one or more of which may be optionally be replaced by heteroatoms selected from N, P, O and S, said chain being optionally substituted by inert substituents, and wherein optionally one or more of said carbon or heteroatom chain members forms part of a ring structure, and pharmaceutically acceptable salt, ester, amide, anhydride or lactone thereof, wherein said therapeutically effective amount of said amphipathic α,α-substituted long-chain dicarboxylic acid is or a pharmaceutically acceptable salt, ester, amide, anhydride or lactone thereof, specifically pharmaceutically acceptable salt, ester or amide thereof, in an amount of from about 10 mg per day to about 200 mg per day. In some specific embodiments administration is oral.

In yet a further, seventh aspect, disclosed herein is a method of treating and/or preventing a pathology, symptom and/or disease associated with type 2 diabetes mellitus in a human subject in need thereof, said method comprising administering to said human subject a therapeutically effective amount of an amphipathic α,α-substituted long-chain dicarboxylic acid of the formula (I):

HOOC—CR$_1$R$_2$-Q-CR$_3$R$_4$—COOH     (I)

wherein

R$_1$, R$_2$, R$_3$ and R$_4$, each independently represents an optionally substituted alkyl, alkenyl, alkynyl, cycloalkyl, aryl, aralkyl or a lower alkoxy group; and Q represents a diradical consisting of a linear chain of 12 to 16 carbon atoms, one or more of which may be optionally be replaced by heteroatoms selected from N, P, O and S, said chain being optionally substituted by inert substituents, and wherein optionally one or more of said carbon or heteroatom chain members forms part of a ring structure, and pharmaceutically acceptable salt, ester, amide, anhydride or lactone thereof, in an amount of from about 10 mg per day to about 200 mg per day. The said pathology, symptom or disease associated with type 2 diabetes mellitus is any one of insulin resistance, hyperglycemia, obesity/overweight, diabetic dyslipidemia, diabetic hyper-triglyceridemia, diabetes-associated neurodegeneration, diabetes macrovascular disease, or diabetes microvascular disease. In some specific embodiments administration is oral.

In a further, eighth aspect, disclosed herein is a method of preventing and/or delaying the onset of type 2 diabetes mellitus or the onset of anti-diabetic treatment in a pre-type 2 diabetic subject, or in an impaired-glucose tolerance (IGT) subject, or in an impaired fasting glucose (IFG) subject, said method, comprising administering to said human subject a therapeutically effective amount of an amphipathic α,α-substituted long-chain dicarboxylic acid of the formula (I):

HOOC—CR$_1$R$_2$-Q-CR$_3$R$_4$—COOH     (I)

wherein

R$_1$, R$_2$, R$_3$ and R$_4$, each independently represents an optionally substituted alkyl, alkenyl, alkynyl, cycloalkyl, aryl, aralkyl or a lower alkoxy group; and Q represents a diradical consisting of a linear chain of 12 to 16 carbon atoms, one or more of which may be optionally be replaced by heteroatoms selected from N, P, O and S, said chain being optionally substituted by inert substituents, and wherein optionally one or more of said carbon or heteroatom chain members forms part of a ring structure, and pharmaceutically acceptable salt, ester, amide, anhydride or lactone thereof, wherein said therapeutically effective amount of said amphipathic α,α-substituted long-chain dicarboxylic acid or pharmaceutically acceptable salt, ester, amide, anhydride or lactone thereof, specifically pharmaceutically acceptable salt, ester or amide thereof, in an amount from about 10 mg per day to about 200 mg per day. In some specific embodiments administration is oral.

In a further ninth aspect, disclosed herein is a method of decreasing insulin resistance, and/or fasting plasma glucose level, and/or blood level of glycosylated hemoglobin A1$_C$, and/or increasing glucose tolerance in a pre-type 2 diabetic or hyperglycemic type 2 diabetes mellitus human subject, comprising administering to said human subject a therapeutically effective amount of an amphipathic α,α-substituted long-chain dicarboxylic acid of the formula (I):

HOOC—CR$_1$R$_2$-Q-CR$_3$R$_4$—COOH     (I)

wherein

R$_1$, R$_2$, R$_3$ and R$_4$, each independently represents an optionally substituted alkyl, alkenyl, alkynyl, cycloalkyl, aryl, aralkyl or a lower alkoxy group; and Q represents a diradical consisting of a linear chain of 12 to 16 carbon atoms, one or more of which may be optionally be replaced by heteroatoms selected from N, P, O and S, said chain being optionally substituted by inert substituents, and wherein optionally one or more of said carbon or heteroatom chain members forms part of a ring structure, and pharmaceutically acceptable salt, ester, amide, anhydride or lactone thereof, specifically pharmaceutically acceptable salt, ester or amide thereof, wherein said therapeutically effective amount of amphipathic α,α-substituted long-chain dicarboxylic acid or pharmaceutically acceptable salt, ester, amide, anhydride or lactone thereof in an amount from about 10 mg per day to about 200 mg per day. In some specific embodiments administration is oral.

In said sixth, seventh, eighth and ninth aspects, insulin resistance of said subject is decreased compared to the insulin resistance of said subject before/without treatment with said amphipathic α,α-substituted long-chain dicarboxylic acid or pharmaceutically acceptable salt, ester, amide, anhydride or lactone thereof, specifically pharmaceutically acceptable salt, ester or amide thereof; and/or the level of fasting plasma/blood glucose of said subject is decreased compared to the fasting plasma/blood glucose of said subject before/without treatment with said amphipathic α,α-substituted long-chain dicarboxylic acid, pharmaceutically acceptable salt, ester, amide, anhydride or lactone thereof, specifically pharmaceutically acceptable salt, ester or amide thereof; and/or the plasma level of glycosylated hemoglobin A1$_C$ of said subject is decreased compared to the plasma level of glycosylated hemoglobin A1$_C$ of said subject before/without treatment with said amphipathic α,α-substituted long-chain dicarboxylic acid, pharmaceutically acceptable salt, ester, amide, anhydride or lactone thereof, specifically pharmaceutically acceptable salt, ester or amide thereof; and/or glucose tolerance of said subject is improved compared to the glucose tolerance of said subject before/without treatment with said amphipathic α,α-substituted long-chain dicarboxylic acid, pharmaceutically acceptable salt, ester, amide, anhydride or lactone thereof, specifically pharmaceutically acceptable salt, ester or amide thereof.

In said sixth, seventh, eighth and ninth aspects, said amphipathic α,α-substituted long-chain dicarboxylic acid or pharmaceutically acceptable salt, ester, amide, anhydride or lactone thereof, specifically pharmaceutically acceptable salt, ester or amide thereof is administered at a dose of from about 10 mg per day to about 200 mg per day, 10 mg per day to about 150 mg per day, 10 mg per day to about 100 mg per day, or 10 mg per day to about 50 mg per day, or once or twice daily. The said amphipathic α,α-substituted long-chain dicarboxylic acid or pharmaceutically acceptable salt, ester, amide, anhydride or lactone thereof, specifically pharmaceutically acceptable salt, ester or amide thereof is administered once, twice or three times weekly. The said amphipathic α,α-substituted long-chain dicarboxylic acid or pharmaceutically acceptable salt, ester, amide, anhydride or lactone thereof, specifically pharmaceutically acceptable salt, ester or amide thereof can be administered chronically. In some specific embodiments administration is oral.

The above disclosed methods of treatment can lead to decrease of insulin resistance of the treated subject compared to the insulin resistance of the subject before administration of amphipathic α,α-substituted long-chain dicarboxylic acid or pharmaceutically acceptable salt, ester, amide, anhydride or lactone thereof, specifically pharmaceutically acceptable salt, ester or amide thereof or without treatment. Furthermore, the above disclosed methods can lead to decrease of plasma level of fasting glucose of the treated subject compared to the fasting plasma glucose of the subject before administration of said amphipathic α,α-substituted long-chain dicarboxylic acid or pharmaceutically acceptable salt, ester, amide, anhydride or lactone thereof, specifically pharmaceutically acceptable salt, ester or amide thereof or without treatment. In addition, the above disclosed methods can lead to decrease of the plasma level of glycosylated hemoglobin A1$_C$ of the treated subject compared to the plasma level of glycosylated hemoglobin A1$_C$ of the subject before administration of said amphipathic α,α-substituted long-chain dicarboxylic acid or pharmaceutically acceptable salt, ester, amide, anhydride or lactone thereof, specifically pharmaceutically acceptable salt, ester or amide thereof or without treatment. Additionally, the above disclosed methods can lead to improvement of glucose tolerance of the treated subject compared to the glucose tolerance of the subject before administration of said amphipathic α,α-substituted long-chain dicarboxylic acid or pharmaceutically acceptable salt, ester, amide, anhydride or lactone thereof, specifically pharmaceutically acceptable salt, ester or amide thereof or without treatment. Where the patient is under ongoing treatment with conventional anti-diabetic drug/s, the treatment disclosed herein can lead to a decrease in dose of and up to obviating need for the conventional treatment.

In all of the above aspects and embodiments of the present disclosure, while administration of the amphipathic α,α-substituted long-chain dicarboxylic acid is primarily oral, other routes of administration are contemplated within the scope of the present disclosure, including, but not limited to parenteral administration, for example intravenous, intramuscular or intraperitoneal administration or intrathecal or subcutaneous injection.

In yet a further aspect, disclosed herein is a kit for achieving a therapeutic effect in a pre-type 2 diabetic or type 2 diabetes mellitus human subject in need thereof, said kit comprising:

a. at least one amphipathic α,α-substituted long-chain dicarboxylic acid of the formula (I):

HOOC—CR$_1$R$_2$-Q-CR$_3$R$_4$—COOH    (I)

wherein the substituents are as defined in claim 1; or pharmaceutically acceptable salt, ester, amide, anhydride or lactone thereof, and optionally a pharmaceutically acceptable carrier or diluent in a first unit dosage form;

b. at least one standard-of-care anti-diabetic drug and optionally pharmaceutically acceptable carrier or diluent in a second unit dosage form;

c. container means for containing said first and second dosage forms;

d. optionally, means for administering said first and second unit dosage forms; and e. instructions for use.

In the disclosed kit, said compound of formula (I) can be any one of 2,2,15,15-tetramethylhexadecane-1,16-dioic acid (also referred to herein as M16αα) or 2,2,17,17-tetramethyloctadecane-1,18-dioic acid (also referred to herein as M18αα) or 2,2,19,19-tetramethyl-docosane-1,20-dioic acid (also referred to herein as M20αα). The said anti-diabetic drug can be metformin, a glitazone, a sulphonylurea, a meglitinide, acarbose, a DPP4 inhibitor, a SGLT2 inhibitor, a GLP1 analog, insulin or an insulin analog, or any mixture of at least two thereof. The said therapeutic effect can be decreasing insulin resistance, and/or fasting blood glucose level, and/or blood level of glycosylated hemoglobin A1$_C$, and/or increasing glucose tolerance in said subject.

In all of the above aspects and embodiments of the present disclosure, the amphipathic α,α-substituted long-chain dicarboxylic acid can specifically be a dicarboxylic acid of the formula HOOC—C(CH$_3$)$_2$—(CH$_2$)$_n$—C(CH$_3$)$_2$—COOH, wherein n is an integer of from 12 to 16. Specifically, the amphipathic dicarboxylic acid is 2,2,15,15-tetramethylhexadecane-1,16-dioic acid (also referred to herein as M16αα) or 2,2,17,17-tetramethyloctadecane-1,18-dioic acid (also referred to herein as M18αα), or 2,2,19,19-tetramethyl-docosane-1,20-dioic acid (M20αα).

DETAILED DESCRIPTION OF PREFERRED EMBODIMENTS

Disclosed are methods for treating Type 2 diabetes (T2D) and/or for treating and/or delaying/preventing a pathology/symptom/disease associated with Type 2 diabetes in humans receiving ongoing standard-of-care (SoC) antidiabetic treatment, by administration of an amphipathic α,α-substituted long-chain dicarboxylic acid of the Formula (I) (hereafter "α,α-substituted dicarboxylic acid" or "ααMedica" or "Mαα" or "a Medica drug"), as defined in detail below, or pharmaceutically acceptable salt, ester, amide, anhydride or lactone thereof. In these embodiments, the α,α-substituted dicarboxylic acid is administered as an add-on treatment to the ongoing SoC treatment. In some specific embodiments administration is oral.

Also disclosed are methods for treating Type 2 diabetes (T2D) and/or for treating and/or delaying/preventing a pathology/symptom/disease associated with Type 2 diabetes in humans by administration of an amphipathic α,α-substituted long-chain dicarboxylic acid of the Formula (I), as defined in detail below, or pharmaceutically acceptable salt, ester, amide, anhydride or lactone thereof, in an amount of from about 10 mg per day to about 200 mg per day. In some specific embodiments administration is oral.

By "Type 2 diabetes" (T2D) as used herein is meant Type 2 diabetes mellitus (T2DM) or non-insulin dependent diabetes mellitus (NIDDM).

By "pathology/symptom/disease associated with Type 2 diabetes" as used herein are meant any one of insulin resistance, hyperglycemia, obesity/overweight, diabetic dyslipidemia, diabetic hypertriglyceridemia, diabetes-associated neurodegeneration, diabetes macrovascular disease (e.g. cardiovascular, cerebrovascular, or peripheral vascular disease) or diabetes microvascular disease (e.g. retinopathy, nephropathy, neuropathy) and any of their combinations, but not limited thereto.

According to currently accepted medical standards, in non-diabetic normoglycemic humans, fasting blood glucose (FBG) levels are ≤110 mg/dL [6.1 mmol/L], 2-hour glucose level in the glucose-tolerance test<140 mg/dL [7.8 mmol/L]. Normal glycosylated hemoglobin (HbA1c) blood levels are <5.7% (DCCT).

Isolated plasma impaired fasting glucose (IFG) levels are ≥110 mg/dL [6.1 mmol/L] and <126 mg/dL [7.0 mmol/L], and 2-hour glucose level in the oral glucose-tolerance test<140 mg/dL [7.8 mmol/L]. Isolated impaired glucose tolerance (IGT) is characterized by 2-hour glucose level in the oral glucose-tolerance test≥140 and <200 mg/dL [11.1 mmol/L] following an oral glucose load of 75 gr. HbA1c levels in both IFG and IGT are 5.7-6.4%. Both IFG and/or IGT define a prediabetes type 2 state, having a 50% risk of converting to T2D in 10 years.

Combined impaired fasting glucose and impaired glucose tolerance is characterized by fasting glucose level≥110 and <126 mg/dL, and 2-hour glucose level in the oral glucose-tolerance test≥140 and <200 mg/dL following an oral glucose load of 75 gr.

Diabetes (herein also referred to as "T2D") is defined by fasting glucose level≥126 mg/dL, 2-hour glucose level in the glucose-tolerance test≥200 mg/dL, or both, HbA1c levels≥6.5%.

Diabetes and prediabetes are two distinct medical conditions, to be approached differently, as detailed below.

Rationale for Using MEDICA

First line therapy for Type 2 Diabetes (T2D), is therapeutic life style change (TLC), namely, weight reduction by dietary measures and physical exercise. However, the poor compliance to behavioral modification measures, being abrogated by genetic disposition, modern life tumult, culture and media-promoted food consumption, and human nature, calls for pharmacological intervention. T2D usually requires the combination of multiple drugs to achieve adequate glycemic, lipemic, hypertensive and body weight control. Thus, T2D patients are normally treated with 5-8 distinct drugs. These are designed to control hyperglycemia (metformin, sulphonylureas, DPP4 inhibitors, GLP1 analogs, acarbose, SGLT2 inhibitors, insulin and insulin analogs), dyslipidemia (statins, ezetimibe, fibrates), obesity and hypertension. However, the multiple drug approach is flawed by higher risk of adverse reactions, complicated treatment protocols and high cost. Moreover, some of the drugs prescribed for T2D may counteract each other, resulting in alleviating a specific T2D component while aggravating some other. The "new diabetes" prompted by some first line drugs used for treating hypertension (e.g., beta-blockers, thiazides), as well as the recently reported increase in diabetic risk in statin users are just two examples. Most importantly, in spite of the major advances made in treating T2D disease aspects, the current success of treating single goals (e.g., glycemic, lipemic, hypertensive profile) is still limited (~50%), while success in overall controlling all goals remains poor (<15%) (Cheung B M, Am J Med 122:443-53 (2009).

These major deficiencies in current pharmacological treatments for the T2D reflect limited understanding of the core molecular targets that drive the various pathological components of T2D. In the absence of an established etiological upstream core targets to be specifically addressed, the prevailing treatment approach essentially consists of treating downstream biomarkers of T2D, like plasma glucose, triglycerides and cholesterol, blood pressure and body weight, while falling short of addressing the upstream etiological drivers of T2D.

In searching for respective etiological core targets for the T2D over the years, the inventor has focused on transcription factors previously reported to control an umbrella expression of genes coding for enzymes and proteins that dominate gluconeogenesis, lipoprotein production, lipoprotein clearance, lipogenesis and lipolysis, as well as genes involved in promoting the inflammatory/atherosclerotic aspects of T2D. This approach has resulted in focusing on the following core targets and their respective cross-talk, namely, AMP-activated protein kinase (AMPK), the mammalian target of rapamycin (mTORC1), the mitochondrial permeability transition pore (PTP), and the four transcription factors, Forkhead box O1 (FoxO1), Hepatocyte nuclear factor 4-alpha (HNF4α), Sterol response element binding protein 1 & 2 (SREBP), and Signal transducer and activator of transcription 3 (STAT3). Most importantly, in contrast to other competitive strategies that search for one and single molecular target, the approach of the present inventor is that the complexity of T2D calls for a set of targets and their respective cross-talk to be concomitantly addressed when searching for a treatment mode for T2D.

Applicant's α,α-substituted long-chain dicarboxylic acids (Medica drugs), for example the current lead compound, 2,2,15,15-tetramethylhexa-decane-1,16-dioic acid (also referred to herein as Medica16αα or M16αα), have been found to modulate the activity of all said concerned targets by activating AMPK while suppressing mTORC1 and the transcriptional activities of HNF4α, FoxO1, SREBP and STAT3. Also, similarly to thyroid hormone, M16αα induces low-conductance gating of mitochondrial PTP resulting in mild decoupling of mitochondrial oxidative phosphorylation with increased energy expenditure. In line with its efficacy in modulating the concerned molecular targets, M16αα has proved statin-like efficacy in lowering plasma LDL-cholesterol, combined with robust decrease of plasma triglycerides in animal models. Also, M16αα has proved to display a potent insulin-sensitizing and glucose-lowering efficacy, combined with increased energy expenditure in animal models for T2D (e.g., db/db rats, rodents maintained on high-fat diet). In light of its preclinical efficacy and safety profile, the M16αα lead has been selected to be further developed as drug for T2D and its related symptoms and diseases, as well as other T2D associated discrete diseases.

Targeting higher up upstream targets of T2D, namely, targets that control the expression and activity of multiple downstream targets, carries the risk of modulating downstream adverse targets that may result in adverse effects. Hence, the M16αα strategy is perhaps more vulnerable to adverse effect risks than treatment modes that specifically address downstream targets. This consideration implies that M16αα doses should be minimized in order to enable reasonable therapeutic window. As will be shown in the experimental section below, it has been found that M16αα significantly improved diabetic profile of a T2D patient not under anti-diabetic SoC, at a low dose.

It has also been found, as presented in the experimental section below, that M16αα was effective as an add-on drug, to patients under anti-diabetic SoC, more than other known antidiabetic drugs.

The Medica-αα Compounds

The Medica-αα drugs are long chain α,α'-disubstituted α,ω-dicarboxylic acids, wherein in some specific embodiments the substituents of the alpha and omega carbon atoms are methyl group.

The exemplary M16αα (current lead compound) is 2,2,15,15-tetramethyl-hexadecane-1,16-dioic acid, having the following chemical structure: HOOC—C(CH$_3$)$_2$—(CH$_2$)$_{12}$—C(CH$_3$)$_2$—COOH. M16αα can be prepared by methods essentially as described in WO98/30530.

As disclosed in WO98/30530, M16αα was found to be a potent hypolipidemic agent in rats, particularly suited for the treatment and prevention of dyslipoproteinemia (combined hypercholesterolemia-hypertriglyceridemia, low HDL-cholesterol). The effects of M16αα in rats were also tested for treatment of impaired glucose tolerance (IGT), leading to T2D. The hypolipidemic effect of M16αα was characterized by decrease in plasma triglycerides and cholesterol in normolipidemic animals and normalization of plasma lipids in hyperlipidemic animal models.

The safety pharmacology of M16αα was evaluated, and the following were studied: hemodynamics (rats); respiratory (rats); Irwin (rats); Telemetry (dogs); Cloned hERG channels; P450 (in vitro). Genetic toxicology was studied (mutagenicity, micronucleus, chromosomal aberration). General toxicology was also evaluated (acute toxicity (rats); oral 4-weeks (rats); MTD (dogs); oral 4-weeks (dogs).

Further information regarding M16αα may be found in the above-mentioned WO 98/30530 hereby incorporated by reference in its entirety.

The compound 2,2,15,15-tetramethylhexadecane-1,16-dioic acid (also designated M16αα), and also the compounds 2,2,17,1,7-tetramethylocta-decane-1,18-dioic acid (M18αα) and 2,2,19,19-tetramethyl-docosane-1,20-dioic acid (M20αα), were tested for their effect on glucose uptake and production, and the expression of glucose- and lipid-related genes in in vitro models. Glucose uptake was measured in fully differentiated 3T3L1 adipocytes, with insulin as positive control, and the compounds were shown to increase glucose uptake. Inhibition of glucose production was tested in HepG2 human liver cells. The tested Medica-αα compounds showed significant or full inhibition of hepatic glucose production and of lipoprotein production in cultured human HepG2 liver cells, and the tested Medica-αα compounds were effective in inhibiting the expression of genes that control liver gluconeogenesis and lipid synthesis.

In addition, the glucose lowering effect of the above three compounds M16αα, M18αα and M20αα was tested in C57BL/KsJ (db/db) Spontaneous T2D mice, which serve as a model for T2D. These animals are characterized by hyperphagia, obesity, hyperglycemia and insulin resistance. The mice were treated once daily by oral administration of the tested compound at 30 mg/kg. The compounds were shown to significantly decrease blood glucose levels, serum insulin levels, and serum triglyceride levels.

Treatment Protocols of the Present Disclosure

The experiments described in WO98/30530 and the above further experiments, showed efficacy of the Medica-αα compounds in animals. The doses used in animals, when extrapolated to humans according to accepted standards would result in very high doses of about 1500-2000 mg/day for a human adult. Although the compounds are not toxic, considering the required chronic administration, in some aspects of the present disclosure, such as treatment of pre-diabetic or diabetic patients that are receiving anti-diabetic SoC treatment, the present inventors have designed new treatment protocols. These treatment protocols use significantly lower doses of the active compounds.

The half-life ($T_{1/2}$) of Medica compounds in humans differs considerably from their half-life in model animals. For example, the half-life of Medica16-ββ (3,3,14,14-tetramethylhexadecanedioic acid) in rats is 2.7±0.4 hours, in dogs 25.8 hours, and in humans 31.5±12.8 hours. M16αα of the present disclosure, the lead compound in the clinical trial presented in the experimental section below, has a half-life of 2.4±0.6 hours in rats, 65 hours in dogs, and 30-80 hours half-life in humans. This difference in half-life could not be expected, and is of considerable significance when designing a new treatment protocol for humans.

It is to be appreciated that the Medica-αα compounds are not designed to decrease glucose or insulin in normoglycemic/normoinsulinemic subjects, whether animals or humans. Rather, they are expected to have efficacy in hyperglycemic hyperinsulinemic subjects, while being devoid of hypoglycemic effect in normal individuals. Once glucose-reducing drugs were first developed, the object was to normalize blood glucose levels in diabetic or prediabetic patients. It has since become known that hypoglycemia is to be avoided, not only because of the risk of a hypoglycemic shock, but also because it may be a risk factor in cardiovascular events.

The results presented in the experimental section below not only exhibit the significant therapeutic effect of M16αα in a low dose treatment protocol in type 2 diabetic subject, but also show its benefit as an add-on drug in the treatment of type 2 diabetic subjects already under anti-diabetic SoC. M16αα added to the SoC protocol of diabetic patients exhibited glucose-lowering activity surpassing those reported for current SoC oral anti-diabetic drugs. Importantly, metformin and pioglitazone are the only anti-diabetic drugs reported to induce sensitization to insulin, while others, like sulphonylurea, meglitinides, DPP4 inhibitors, GLP1 analogs and SGLT2 inhibitors are all devoid of an insulin-sensitizing activity. As shown in the results below, also the insulin sensitizing activity of M16αα added-on to metformin surpasses that of add-on pioglitazone. The exhibited beta-cell rest by M16αα, combined with its robust insulin-sensitizing activity may also be predictive of its efficacy in maintaining long-term beta-cell function in T2D patients. The insulin-sensitizing activity of M16αα combined with its activity in lowering plasma insulin may predict alleviation of the non-glycemic diseases of T2D. In accordance with the surprising results shown herein, it is expected that M16αα may offer an All-in-One treatment mode for T2D patients, avoiding the higher risk of adverse reactions, complicated treatment protocols and high cost of the multiple drug approach to the treatment of T2D. In addition, M16αα may offer a First-in-Line drug for treating the Metabolic Syndrome.

In addition, the present treatment protocols may be particularly useful for treating prediabetic patients (as defined above), to prevent/delay the development of T2D in prediabetic IGT/IFG patients.

The Examples below present the results of clinical studies, conducted on males and post-menopausal women.

Based on the results presented below, it is also suggested that a particular dosage range may be highly effective with regard to the patients' response to treatment, as verified by various clinical endpoints. Doses above said range may likely not increase efficacy, and in some cases may even decrease efficacy (depending on the individual patient, indication to be treated and other factors), while over time, such higher doses may result in undesirable side-effects stemming from high prolonged exposure to the drug.

In a first aspect, the present disclosure is concerned with the treatment of Type 2 diabetes in a human subject receiving anti-diabetic SoC, by administering to the subject an amphipathic α,α-substituted long-chain dicarboxylic acid of Formula (I), as presented below, or a pharmaceutically acceptable salt, ester, amide, anhydride or lactone thereof. In some specific embodiments administration is oral.

In a second aspect, the present disclosure is concerned with treating and/or preventing a pathology/symptom/disease associated with Type 2 diabetes in a human subject receiving anti-diabetic SoC, by administering to the subject an amphipathic α,α-substituted long-chain dicarboxylic acid of Formula (I), as presented below, or a pharmaceutically acceptable salt, ester, amide, anhydride or lactone thereof. The said pathology/symptom/disease associated with type 2 diabetes may be any and at least one of insulin resistance, hyperglycemia, obesity/overweight, diabetic dyslipidemia, diabetic hypertriglyceridemia, obesity, overweight, diabetes-associated neuro-degeneration diabetes macrovascular disease (e.g. cardiovascular, cerebrovascular, peripheral vascular) or diabetes microvascular disease (e.g. retinopathy, nephropathy, neuropathy). In some specific embodiments administration is oral.

In both said first, and second aspects of the present disclosure, the standard-of-care (SoC) treatment is at least one of therapeutic life style change (TLC) or treatment with at least one topical, oral or parenteral anti-diabetic drug, which may be any hypoglycemic drug, including insulin sensitizers, such as metformin or a glitazone (e.g. rosiglitazone, pioglitazone) or insulin secretagogues, such as a sulphonylurea or a meglitinide, but not limited thereto. The anti-diabetic drug may also be a GLP1 analog, a DPP4 inhibitor or a SGLT2 inhibitor, or the anti-diabetic drug may be insulin or an insulin analog.

In yet a third aspect, the present disclosure is concerned with a method for maintaining or reducing standard-of-care (SoC) administered dose of an anti-diabetic drug, or for obviating the need for administration of such drug in a type 2 diabetic subject, by administration of an amphipathic α,α-substituted long-chain dicarboxylic acid of Formula (I), as presented below, or a pharmaceutically acceptable salt, ester, amide, anhydride or lactone thereof. Also in this aspect, the anti-diabetic drug may be any hypoglycemic drug, including insulin sensitizers, such as metformin or a glitazone (e.g. rosiglitazone, pioglitazone) or insulin secretagogues, such as a sulphonylurea or a meglitinide, but not limited thereto. The anti-diabetic drug may also be an incretin, such as a GLP1 analog or a DPP4 inhibitor, or it may be a SGLT2 inhibitor, or the anti-diabetic drug may be insulin or an insulin analog. In some specific embodiments administration is oral.

In a further, fourth aspect, the present disclosure is concerned with a method of preventing or delaying the onset of anti-diabetic treatment in a pre-diabetic subject, or in an impaired-glucose tolerance (IGT) subject, or in an impaired fasting glucose (IFG) subject, wherein said subject receives anti-diabetic standard-of-care (SoC) treatment, said method comprising administering to said subject an amphipathic α,α-substituted long-chain dicarboxylic acid of formula (I), a detailed below, or a pharmaceutically acceptable salt, ester, amide, anhydride or lactone thereof. The SoC may be Therapeutic lifestyle change (TLC) and/or treatment with an anti-diabetic drug, which may be any hypoglycemic drug, including insulin sensitizers, such as metformin or a glitazone, e.g. rosiglitazone, or insulin secretagogues, such as a sulphonylurea or a meglitinide, but not limited thereto. The anti-diabetic drug may also be an incretin, such as a GLP1 analog or a DPP4 inhibitor, or it may be a SGLT2 inhibitor. In some specific embodiments administration is oral.

In yet a further aspect, the present disclosure is concerned with a method of decreasing insulin resistance, and/or fasting plasma glucose level, and/or plasma level of glycosylated hemoglobin, and/or increasing glucose tolerance in pre-type 2 diabetic or a hyperglycemic type 2 diabetes human subject, wherein said subject receives anti-diabetic standard-of-care (SoC) treatment, comprising administering to said human subject an amphipathic α,α-substituted long-chain dicarboxylic acid of Formula (I) as detailed below, or pharmaceutically acceptable salt, ester, amide, anhydride or lactone thereof The anti-diabetic standard of care treatment may be Therapeutic lifestyle change (TLC) and/or treatment with an anti-diabetic drug, which may be any hypoglycemic drug, including insulin sensitizers, such as metformin or a glitazone, e.g. rosiglitazone, or insulin secretagogues, such as a sulphonylurea or a meglitinide, but not limited thereto. The anti-diabetic drug may also be an incretin, such as a GLP1 analog or a DPP4 inhibitor, or it may be a SGLT2 inhibitor. In some specific embodiments administration is oral.

In yet a further aspect, the present disclosure is concerned with treating Type 2 diabetes in a human subject in need thereof, comprising administering to the subject an amphipathic α,α-substituted long-chain dicarboxylic acid of Formula (I), as presented below, or a pharmaceutically acceptable salt, ester, amide, anhydride or lactone, in an amount of from about 10 mg to about 200 mg per day. In some specific embodiments administration is oral.

In yet a further aspect, the present disclosure is concerned with treating and/or preventing a pathology/symptom/disease associated with Type 2 diabetes in a human subject, by administering to the subject an amphipathic α,α-substituted long-chain dicarboxylic acid of Formula (I), as detailed below, or a pharmaceutically acceptable salt, ester, amide, anhydride or lactone thereof in an amount of from about 10 mg per day to about 200 mg per day. The said pathology/symptom/disease associated with type 2 diabetes may be any and at least one of insulin resistance, hyperglycemia, obesity/overweight, diabetic dyslipidemia, diabetic hypertriglyceridemia, obesity, overweight, diabetes-associated neurodegeneration diabetes macrovascular disease (e.g. cardiovascular, cerebrovascular, peripheral vascular) or diabetes microvascular disease (e.g. retinopathy, nephropathy, neuropathy). In some specific embodiments administration is oral.

In a further aspect, the present disclosure is concerned with a method of preventing or delaying the onset of anti-diabetic treatment in a pre-diabetic subject, or in an impaired-glucose tolerance (IGT) subject, or in an impaired fasting glucose (IFG) subject, said method comprising administering to said subject an amphipathic α,α-substituted long-chain dicarboxylic acid of Formula (I), as detailed below, or a pharmaceutically acceptable salt, ester, amide, anhydride or lactone thereof in an amount of from about 10 mg per day to about 200 mg per day. In some specific embodiments administration is oral.

In a further aspect, the present disclosure is concerned with a method of preventing and/or delaying the onset of type 2 diabetes mellitus in a human subject susceptible thereto, the method comprising administering to said human subject an amphipathic α,α-substituted long-chain dicarboxylic acid or pharmaceutically acceptable salts, esters, amides, anhydrides or lactones thereof, in an amount from about 10 mg per day to about 200 mg per day. In some specific embodiments administration is oral. A non-limiting example of a human subject susceptible to developing pre type 2 diabetes or type 2 diabetes is a patient diagnosed with the Metabolic Syndrome. A patient diagnosed with the Metabolic Syndrome has at least three of the following: abdominal obesity, hypertriglyceridemia, low HDL-cholesterol, hypertension, hyperglycemia. Hence, a Metabolic Syndrome patient may be susceptible to T2D, although at times, this patient does not exhibit all of the Pre-Diabetes criteria as defined herein, namely exhibiting impaired HbA1C, impaired glucose tolerance (IGT) or impaired fasting glucose (IFG) levels. Thus, while a Metabolic Syndrome patient is not necessarily hyperglycemic (namely T2D) or pre-diabetic (in terms of HbA1C, IGT, IFG), since he is at risk for proceeding on to T2D he is recommended to start on TLC and/or metformin treatments.

In yet a further aspect, the present disclosure is concerned with a method of decreasing insulin resistance, and/or fasting plasma glucose level, and/or plasma level of glycosylated hemoglobin, and/or increasing glucose tolerance in pre-diabetic or type 2 hyperglycemic diabetes human subject, comprising administering to said human subject an amphipathic α,α-substituted long-chain dicarboxylic acid of Formula (I), as detailed below, or pharmaceutically acceptable salt, ester, amide, anhydride or lactone thereof in an amount from about 10 mg per day to about 200 mg per day. In some specific embodiments administration is oral.

In all aspects and embodiments of the present disclosure, the said symptom, disease, condition or pathology in Type 2 diabetes or pre-diabetes is any one of insulin resistance, hyperglycemia, obesity/overweight, diabetic dyslipidemia, diabetic hypertriglyceridemia, diabetes-associated neuro-degeneration, diabetes macrovascular disease (cardiovascular, cerebrovascular, peripheral vascular) or diabetes microvascular disease (retinopathy, nephropathy, neuropathy). Treatment of T2D or any of its said associated pathologies/symptoms/diseases is also beneficiary to other discrete diseases, such as T2D-associated cancer or T2D neurodegeneration.

Where diabetic dyslipidemia is concerned, the methods of the invention may be intended for any or all of the following: elevating the plasma level of HDL-cholesterol, for example by at least 5%, at least 10%, at least 15%, at least 20%, at least 25%, or even at least 30% or 35% as compared to the level prior to treatment with a Medica drug; additionally, the plasma level of HDL-cholesterol may be elevated above at least 30 or 40 mg/DL; further, the method may comprise maintaining the plasma level of HDL-cholesterol above the level prior to the treatment with a Medica drug by the percentages described above and/or above 30 or 40 mg/DL; decreasing the plasma level of LDL-cholesterol for example by at least 5%, at least 10%, at least 15%, at least 20%, at least 25%, at least 30%, at least 40%, at least 50% or even at least 55 or 60% as compared to the level prior to treatment with a Medica drug; additionally, the plasma level of LDL-cholesterol may be decreased below at least 190 mg/DL, at least 160 mg/DL, at least 130 mg/DL or even at least 100 mg/DL; further, the method may comprise maintaining the plasma level of LDL-cholesterol below the level prior to the treatment with a Medica drug by the percentages described above and or below the values described above; decreasing the plasma level of VLDL-cholesterol, for example by at least 5%, at least 10%, at least 20%>, at least 25%>, or even at least 30% or 35%> as compared to the level prior to treatment with a Medica drug; further, the method may comprise maintaining the plasma level of VLDL-cholesterol below the level prior to the treatment by these percentages; decreasing the plasma level of total cholesterol, for example by at least 10%), at least 15%, at least 20%, at least 25%, at least 30%, at least 40%, at least 50% or even at least 55 or 60% as compared to the level prior to treatment with a Medica drug; additionally, the plasma level of total cholesterol may be decreased below at least 240 mg/DL or at least 200 mg/DL; further, the method may comprise maintaining the plasma level of total cholesterol below the level prior to the treatment with a Medica drug by the percentages described above and/or below the values described above; decreasing the plasma level of triglycerides, for example by at least 7%, at least 10%, at least 15%, at least 20%, at least 25%, at least 30%, at least 40%, at least 50% or even at least 55 or 60% as compared to the level prior to treatment with a Medica drug, additionally, the plasma level of triglycerides may be decreased below at least 200 mg/DL or at least 150 mg/DL; further, the method may comprise maintaining the plasma level of cholesterol below the level prior to the treatment with a Medica drug by the percentages described above and/or below the values described above.

In all the above aspects and embodiments of the present disclosure, the disclosed methods comprise decreasing the area under the curve (AUC) of the 2-hours glucose-tolerance test of the treated human subject for example by at least 5%, at least 10%, at least 15%, at least 20%, or at least 25%, as compared to the level prior to treatment with a Medica drug; additionally, the disclosed methods comprise of decreasing the 2-hours glucose level in the oral glucose-tolerance test of the treated human subject for example by at least 5%, at least 10%, at least 15%, at least 20%, or at least 25%, as compared to the level prior to treatment with a Medica drug, or to less than 140 mg/dL; further, the method may comprise of decreasing the plasma glucose level of the 2-hours glucose-tolerance test of the treated human subject by the percentages described above and/or below 140 mg/DL; additionally, the disclosed methods comprise of decreasing the plasma level of fasting blood glucose of the treated subject for example by at least 5%, at least 10%, at least 15%, at least 20%, or at least 25%, as compared to the level prior to treatment with a Medica drug, or to optionally below 126 mg/dL or 110 mg/dL; additionally, the disclosed methods comprise of decreasing the plasma level of glycosylated hemoglobin (HbA1c) for example by least 2.0, at least 4.0, at least 8.0, at least 12.0, or at least 16.0 mmole/mole, as compared to the level prior to treatment with a Medica drug; or to HbA1C below 7.0%, for example to below 6.5%, 6%, or 5.5%. It is to be noted that whereas blood/plasma glucose refers to glucose levels prevailing at the time of sampling, blood HbA1c serves as biomarker for plasma glucose level prevailing throughout the 90-120 day period preceding sampling. Of note, due to the linear progressive glycosylation of HbA1C by blood glucose throughout the 90 days of the erythrocytes' survival in blood, drug effects on HbA1C level following 30 days of treatment, may be extrapolated linearly to estimated drug effect following 120 days of treatment [Hirst J A, et al., PLoS One. 25:9: e92458 (2014).; Beltran Del Rio M, J Diabetes Sci Technol. 10:1303-1307 (2016)]; additionally, the disclosed methods comprise of increasing the hepatic and/or composite Insulin sensitization index (ISI) [Matsuda M & De Fronzo R A, Diabetes Care, 22: 1462-70 (1999)], for example by at least 25%, at least 50%, at least 100%, at least 200% as compared to the level prior to treatment with a Medica drug; additionally, the disclosed methods comprise of decreasing the HOMA insulin resistance (HOMAIR) for example by at least 25%, at least 50%, at least 75%, at least 100% as compared to the level prior to treatment with a Medica drug. The term "level" as used herein, unless indicated differently means plasma or blood levels.

As used herein, the term "prior to the treatment with a Medica drug (as defined herein)" is to be taken to mean either stand-alone treatment with a Medica drug or treatment with Medica drug as Add-On to anti-diabetic SoC treatment, as defined herein.

Where the pathology/symptom associated with diabetes is obesity/overweight, treatment in accordance with the present disclosure may lead to weight loss of the treated patient.

By the term "treat" as used herein, or forms thereof as herein defined, is meant to prevent worsening, or arrest, or alleviate, or improve, or cure the subject's disease or condition, specifically pre-type 2 diabetes mellitus, type 2 diabetes mellitus, Metabolic Syndrome, or pathology or symptom associated with and/or manifested in pre-diabetes mellitus and/or type 2 diabetes mellitus subjects, including, but not limited to, maintaining or reducing insulin resistance, and/or maintaining or increasing glucose tolerance, and/or maintaining or reducing plasma/blood level of at least one of fasting glucose and HbA1c.

The term "treat" as used herein is also to be taken to mean preventing and/or delaying the onset of type 2 diabetes mellitus or the onset of anti-diabetic treatment in a pre-type 2 diabetic subject, or in an impaired-glucose tolerance (IGT) subject, or in an impaired fasting glucose (IFG) subject.

The term "treat" as used herein is also to be taken to mean maintaining or reducing the level of standard of care treatment in a human subject under conventional standard of care treatment with at least one conventional anti-diabetic drug.

The term "human subject in need" as used herein is to be taken to mean a human suffering from pre-type 2 diabetes or type 2 diabetes, or the Metabolic Syndrome. The terms "subject" and "patient" may be used herein alternatingly.

The terms "plasma" and "blood" levels (of any parameter) may be used herein alternatingly.

The term "antidiabetic standard of care (or SoC)" as used herein is to be taken to mean at least one of Therapeutic Lifestyle Change (TLC) (advocating dietary measures and physical exercise) and treatment with at least one topically, orally or parenterally administered anti-diabetic drug, including metformin, glitazones, sulphonylureas, meglitinides, acarbose, DPP4 inhibitors or SGLT2 inhibitors, GLP1 analogs, insulin or insulin analogs.

The term "maintaining" as used herein for levels of one or several parameters, jointly or separately, is to be taken to mean avoiding increase (or decrease where relevant) of the level of the parameter/s before beginning treatment with a Medica drug (or without such treatment), avoiding increase of required dose/s of ongoing standard of care drug/s. By way of non-limiting example, "maintaining standard of care (SoC) administered dose of an anti-diabetic drug" is to be taken to mean that following beginning of treatment with add-on Medica drug, it is not necessary to increase the dose of the SoC drug, for example insulin.

The term "therapeutically effective amount" as used herein is to be taken to mean that amount of a Medica drug which will elicit the required beneficiary biological/medical response in the treated subject human, for example the response sought by a physician or other clinician.

In all aspects and embodiments of the present disclosure, the said amphipathic α,α-substituted long chain dicarboxylic acid is a dicarboxylic acid of the formula (I):

HOOC—CR$_1$R$_2$-Q-CR$_3$R$_4$—COOH          (I)

wherein

R$_1$, R$_2$, R$_3$ and R$_4$, each independently represents an optionally substituted alkyl, alkenyl, alkynyl, cycloalkyl, aryl, aralkyl or a lower alkoxy group; and Q represents a diradical consisting of a linear chain of 12 to 16 carbon atoms, one or more of which may be optionally be replaced by heteroatoms selected from N, P, O and S, said chain being optionally substituted by inert substituents, and wherein optionally one or more of said carbon or heteroatom chain members forms part of a ring structure, and pharmaceutically acceptable salt, ester, amide, anhydride or lactone thereof.

In specific embodiments Q is a straight polymethylene chain of 12-16 carbon atoms.

In specific embodiments, each of R$_1$-R$_4$ is a lower alkyl, such as methyl and ethyl, or lower alkoxy, such as methoxy or ethoxy.

In all aspects and embodiments of the present disclosure, the said amphipathic α,α-substituted long chain dicarboxylic acid is specifically a dicarboxylic acid of the formula (II)

HOOC—C(CH$_3$)$_2$—(CH)$_n$—C(CH$_3$)$_2$—COOH          (II)

wherein n is an integer of from 12 to 16, a pharmaceutically acceptable salt, ester or amide thereof. More specifically, said dicarboxylic acid is 2,2,15,15-tetramethyl-hexadecane-1,16-dioic acid (also referred to herein as M16αα) or 2,2,17,17-tetramethyl-octadecane-1,18-dioic acid (also referred to herein as M18αα), or 2,2,19,19-tetramethyl-docosane-1,20-dioic acid (M20αα).

In all aspects and embodiments of the present disclosure, when referring to "a compound of Formula (I), or a compound of Formula (II), or "a Medica Drug" or "M16αα" or "M18αα" or "M20αα", these terms are to be taken to also encompass pharmaceutically acceptable salt, ester, amide, anhydride or lactone thereof, specifically salt, ester or amide thereof.

In some embodiments, the said salt of said dicarboxylic acid of Formula (I) or Formula (II) is a salt with an inorganic or organic cation, in particular alkali metal salt, alkaline earth metal salt, ammonium salt and substituted ammonium salt; said ester is a lower alkyl ester; said an amide, is a mono- and di-substituted; said anhydride, is an anhydride with a lower alkanoic acid; and/or said lactone is formed by ring closure of either or both carboxylic groups with a free hydroxy substituent (or substituents) in the molecule of formula (I).

In all aspects and embodiments of the present disclosure, as described herein, the dosage of the amphipathic α,α-substituted long chain dicarboxylic acid (also referred to as Medica-αα compound), specifically M16αα, may be from about 10 mg per day to about 200 mg per day, for example 10-175, 10-150, 10-100, 10-50, 20-175, 20-150, 20-100, 20-50, 25-175, 25-150, 25-100, 25-50, 10-175, 30-150, 30-100, 30-50, e.g. 10, 20, 25, 30, 35, 40, 45, 50, 60, 70, 80, 90, 100, 120, 150, or 175 mg/day.

In all aspects and embodiments of the present disclosure, as described herein, the periodic administration may be once daily, twice daily, three times daily, once, twice or three times weekly, or administration may be chronic.

The advantages of lower doses are evident to those of skill in the art. These include, inter alia, a lower risk of side effects, especially in long-term use, and a lower risk of the patient becoming desensitized to the treatment.

The treatment of different conditions may indicate the use of different doses or different time periods, which will be evident to the skilled medical practitioner. For example, lowering plasma glucose, lowering plasma triglycerides, lowering plasma LDL-cholesterol and/or plasma VLDL-cholesterol, lowering plasma total cholesterol, lowering plasma LDL-cholesterol and elevating plasma HDL-cholesterol may be effected by using doses of the active compound, specifically M16αα, in the range of from about 10 mg per day to about 200 mg per day, while treatment of other adverse indications may be effected using doses in the range of from about 10 mg per day to about 50, 100 or 150 mg per day. When the subject in need of treatment is a woman, dosing, frequency and length of period of treatment may vary. Differences in the dosage regimen between males and females may also vary according to the condition to be treated, as described above.

It is to be understood that the minimal/maximal values of the various characteristic parameters to be measured, as indicated herein, may change from time to time according to the definitions and/or guidelines of the FDA.

The effective daily amount of the active Medica drug (compound of Formula (I)), specifically M16αα, is preferably comprised within one dosage unit form, which significantly improves patient's compliance. Alternatively, a dosage unit form may comprise half of the daily required/recommended amount, or other amounts. Dosage unit forms may comprise, in addition to the active Medica drug, pharmaceutically acceptable excipients, carriers, diluents and the like. For oral administration, dosage forms may be in the form of tablets, capsules, caplets and lozenges.

It should be noted that the treatment of different conditions may indicate the use of different doses or different treatment time periods, which will be evident to the skilled medical practitioner.

While the active Medica drug, specifically M16αα, are primarily administered orally according to the methods of the present invention, other modes of administration are contemplated, including, but not limited to parenteral, for example intravenous, intramuscular or intraperitoneal administration or intrathecal or subcutaneous injection. It is to be noted that in those aspects and embodiments of the present disclosure where the patient is treated with the Medica drug in addition to anti-diabetic SoC drug/s, the disclosed Medica drug and said anti-diabetic SoC drug/s are administered simultaneously, or at different time points, at different intervals between administrations, for different durations of time, or in a different order, and via identical or different routes of administration.

The Medica drugs and anti-diabetic SoC drugs used in the methods disclosed herein, can be comprised in a kit, together with, for example, means for their administration and instructions for use.

Thus, in yet a further aspect, disclosed herein is a kit for achieving a therapeutic effect in a pre-type 2 diabetic or type 2 diabetes mellitus human subject in need thereof. The kit comprises (i) at least one amphipathic α,α-substituted long-chain dicarboxylic acid of the formula (I), wherein the substituents are as defined above, or pharmaceutically acceptable salt, ester, amide, anhydride or lactone thereof, specifically salt, ester or amide thereof, and optionally a pharmaceutically acceptable carrier or diluent in a first unit dosage form, for example but not limited to a tablet or soft gel capsule; (ii) at least one standard-of-care anti-diabetic drug, and optionally pharmaceutically acceptable carrier or diluent in a second unit dosage form; (iii) container means for containing said first and second dosage forms; optionally (iv) means for administering said first and second unit dosage forms; and (v) instructions for use. The kit can be designed for use by an attending clinician or medical staff member, or by the patient himself.

In the disclosed kit, said compound of formula (I) can be 2,2,15,15-tetramethylhexadecane-1,16-dioic acid (also referred to herein as M16αα) or 2,2,17,17-tetramethyloctadecane-1,18-dioic acid (also referred to herein as M18αα), or 2,2,19,19-tetramethyl-docosane-1,20-dioic acid (also referred to herein as M20αα). The said anti-diabetic drug is any one of metformin, a glitazone, a sulphonylurea, a meglitinide, acarbose, a DPP4 inhibitor, a SGLT2 inhibitor, a GLP1 analog, insulin or an insulin analog, or any mixture of at least two thereof. The said therapeutic effect can be at least one of decreasing insulin resistance, and/or fasting blood glucose level, and/or blood level of glycosylated hemoglobin $A1_C$, and/or increasing glucose tolerance in said subject.

The said container means for containing both said Medica drug, optionally together with a pharmaceutically acceptable carrier diluent, and said anti-diabetic SoC drug, or optionally together with a pharmaceutically acceptable carrier diluent, can be, for example a separate container for each said drug, or a divided container, such as a divided bottle a divided foil packet, or, where suitable, the separate drugs can be contained within a single, undivided container. Typically, the kit includes instructions for use for the administration of each of the separate drugs. The kit form can be specifically advantageous when the separate components are to be administered in different dosage forms (e.g., oral and parenteral), at different dosage intervals, or when titration of any of the individual drugs is desired by the prescribing physician.

It should be further noted that for the methods of treatment and prevention provided herein, said therapeutic effective amount, or dosage, is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can readily determine optimum dosages, dosing methodologies and repetition rates. In general, dosage is calculated according to body weight. Sustained-release formulations are also contemplated, which provide for the frequent administration. Following successful treatment, it may be desirable to have the patient undergo maintenance therapy to prevent the recurrence of the disease state, wherein the active principal used in the method of the invention is administered at maintenance doses and frequency of administration.

The invention has been described in an illustrative manner, and it is to be understood that the terminology which has been used is intended to be in the nature of words of description rather than of limitation. Modifications and variations of the present invention are possible in light of the above teachings. It is, therefore, to be understood that within the scope of the appended claims, the invention can be practiced otherwise than as specifically described.

The presently disclosed subject matter is further illustrated by the following examples, which are illustrative only and are not to be construed as limiting the scope of the invention. Variations and equivalents of these examples will be apparent to those skilled in the art in light of the present disclosure, the drawings and the claims herein.

It is appreciated that certain features of the presently disclosed subject matter which are, for clarity, described in the context of separate embodiments, may also be provided in combination in a single embodiment. Conversely, various features of the presently disclosed subject matter, which are, for brevity, described in the context of a single embodiment, may also be provided separately or in any suitable subcombination.

Although the presently disclosed subject matter has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent and patent application was specifically and individually indicated to be incorporated herein by reference. In addition, citation or identification of any reference in this application shall not be construed as an admission that such reference is available as relevant prior art to the presently disclosed subject matter.

EXPERIMENTAL

General Description

Exploratory, double-blind, randomized, placebo-controlled study, to evaluate the safety, efficacy and pharmacokinetics of 4-week M16αα treatment of Type 2 Diabetes Mellitus (T2D) patients. T2D patients were either non-treated or receiving ongoing treatment with metformin alone or in combination with other standard-of-care (SoC) oral or parenteral antidiabetic drug/s.

Objectives

1. To obtain preliminary information on safety and efficacy of multiple dose administrations of M16αα to naïve Type 2 Diabetes Mellitus (T2D) patients or T2D patients stabilized on anti-diabetic SoC drugs (all patients uncontrolled—HbA1c>7.3%).

2. To study the effect of M16αα on pharmacodynamic (PD) parameters following multiple M16αα administrations to naïve Type 2 Diabetes Mellitus (T2D) patients or T2D patients stabilized on anti-diabetic drugs.

Study Outcome Measures:

1. Incidence and characteristics of adverse events.
2. Changes from baseline in fasting blood glucose, insulin, HOMA and Hepatic Insulin Sensitivity Index (Hepatic ISI) levels after 4 weeks' treatment.
3. Changes from baseline in Composite Insulin Sensitivity Index (Composite ISI) and Insulin Resistance (IR) during oral glucose tolerance test (OGTT) after 4 weeks' treatment.
4. Changes from baseline in HbA1C after 4 weeks' treatment.
5. Changes from baseline of Continuous Glucose Monitoring System (CGMS) after 4 weeks' treatment.
6. Changes from baseline in plasma lipids (triglycerides, cholesterol, LDL-C, VLDL-C, HDL-C, non-HDL-C, apoB) after 4 weeks' treatment.

Study Design

The study, followed a pilot single-ascending-dose study carried out in healthy volunteers. The study was conducted at the Diabetes Clinic, Wolfson Medical Center (WMC), Holon, Israel and at the Diabetes Medical Center (DMC), Tel Aviv, Israel.

T2D patients, non-treated or treated with SoC antidiabetic drugs as outlined below, were screened for eligibility (inclusion/exclusion according to criteria detailed below), followed by being randomly allocated to receive once daily either add-on M16αα (40 mg M16αα plus 130 mg microcrystalline cellulose in gelatin capsules) or add-on placebo (130 mg microcrystalline cellulose in gelatin capsules), in addition to the SoC anti-diabetic treatment they have been receiving regularly. One patient was not under SoC anti-diabetic drug treatment. Sixteen (16) patients were randomized to M16αα treatment and 3 patients were randomized to placebo treatment. Patients randomized to M16αα treatment were dosed for 28 days with add-on M16αα in double-blinded manner, followed by 4-week recovery period using add-on placebo in a single-blinded manner. Patients randomized to placebo treatment were dosed for 28 days with add-on placebo in double-blinded manner.

Three cohorts participated in this study:

Cohort 1 included 6 uncontrolled T2D patients (HbA1c>7.3%), 5 treated for their hyperglycemia by metformin only (patients 101, 102, 103, 105, 106), and one naïve patient (not under SoC anti-diabetic treatment, patient 108).

Cohort 2 included 6 T2D patients (HbA1c>7.3%) (patients 202, 203, 205, 206, 207, 210) treated for their hyperglycemia by a variety of SoC anti-diabetic drug/s except insulin/insulin analogs (metformin plus sulphonylurea and/or DPP4 inhibitor and/or GLP1 analog and/or SGLT2 inhibitor).

Cohort 3 included 4 T2D patients (HbA1c>7.3%) treated for their hyperglycemia by basal insulin analogs and a variety of anti-diabetic drugs (metformin and/or sulphonylurea and/or DPP4 inhibitor and/or GLP1 analog and/or SGLT2 inhibitor).

Placebo group included 3 patients (104, 107, 208). Patient 107 was not under SoC anti-diabetic treatment.

During the study period the subjects underwent physical examination, clinical pathology, hematology, urinalysis, lipid profile, HbA1C, continuous glucose monitoring (CGM) and an oral glucose tolerance test (OGTT) (75 g glucose; glucose, insulin, c-peptide; 0, 30, 60, 120, 180 min) prior to dosing, upon end of M16αα treatment, and following the recovery period (EOS visit).

Inclusion Criteria

Male 18-80 (inclusive) years old; postmenopausal women, younger than 80 years old (inclusive) not on hormone-replacement therapy (HRT); Diagnosed with T2D, treated with diet and exercise and/or oral or parenteral antidiabetic drug/s; (dose and regimen stable for the 3 months preceding the study); body mass index 26≤BMI≤35 kg/m$^2$, HbA1c>7.3% (inclusive) at screening; LDL-C>75 mg/dL.

Exclusion Criteria

Severe diabetic retinopathy, nephropathy or neuropathy; suffered from a cardiovascular event (e.g. MI, PTCA) in the last year preceding the study or have a chronic cardiovascular condition; known drug or alcohol abuse; positive Hepatitis B or Hepatitis C serology tests; documented history or ongoing symptoms of any gastrointestinal disorder involving motility, gastric acid or gastric emptying or malabsorption, including but not limited to, peptic ulcer disease, gastroesophageal reflux, dyspepsia, gastroparesis, chronic diarrhea, chronic constipation, gall bladder disease, pancreatitis and celiac disease; cancer; uncontrolled hypertension; known history of significant medical disorder, which, in the investigator's judgment, contraindicates administration of the study medications; clinically significant laboratory tests at screening which, in the investigator's judgment, contraindicates administration of the study medications; significant allergic response to other drugs; use of any prescription or over-the-counter (OTC) medications which may contraindicate administration of the study medications; blood donation or receipt in the 3 months preceding the study; participation in another clinical trial in the 30 days preceding the study.

Safety and Tolerability Assessments

The primary safety endpoint was the frequency, severity, and duration of adverse events (AEs), including clinically significant laboratory abnormalities after administration of M16αα.

Safety was evaluated on the basis of the following assessments: Adverse events (AEs)—continuous (starting from informed consent signature until end of study); vital signs; 12-lead ECG; physical examination; safety laboratory evaluations (blood and urine).

PD Evaluation:

HbA1c, Continuous glucose monitoring (CGMS), OGTT (Glucose/Insulin/C-peptide), HOMA, Hepatic Insulin Sensitization Index (HP ISI), Composite insulin sensitization index (Comp ISI), Insulin resistance (IR), plasma lipid profile (Triglycerides, Cholesterol, LDL-C, VLDL-C, HDL-C, non-HDL-C, apoB), hsCRP, Fibrinogen.

PK Evaluation:

Pre-dose blood samples to determine trough levels of M16αα were collected in lithium heparin tubes at the following dosing days: 1, 8, 15, 28, and EOS visit. Plasma M16αα concentrations have been presently processed for Cohort 1 patients only. In line with the long half-life of M16αα (30-80 h), trough M16αα concentrations in each patient increased progressively throughout the 28-day dosing period, reaching Cmax upon end of M16αα dosing. Recovery period resulted in decrease in M16αα plasma concentrations, but still leaving M16αα traces during EOS visit. Calculated PK parameters: Pre-dose $C_{ss}$.

Statistical Analysis:

All measured variables and derived parameters were listed individually and tabulated by descriptive statistics. For descriptive statistics summary tables were provided giving sample size, means, standard deviations and 95% CI (Confidence Interval) or frequency with percentage according to the scale of the variable. Regarding small sample size, non-parametric methods were conducted: Differences between end of drug dosing and baseline for each efficacy parameter were analyzed using the Wilkcoxon matched-pairs signed-ranks test. Differences between M16αα-treated and placebo groups were analyzed for each efficacy parameter using the Mann-Whitney two-sample U-test.

Bioanalytical Analysis:

Plasma concentrations of M16αα are determined by a validated LC/MS method. The lower and upper limits of quantitation for M16αα concentrations are 100 ng/mL and 5000 ng/mL, respectively. The assay is linear from 0.1-5 µg/mL. Dilution extends the range to 100 µg/mL Screening: T2D patients were screened for eligibility within 28 days before first dosing. Eligible subjects underwent a Lead-In period of 3 weeks. During the Lead-In period subjects underwent CGMS and an oral glucose tolerance test.

Drug: 40 mg 2,2,15,15-tetramethylhexadecane-dioic acid (M16αα) per day, in a gelatin capsule. This daily dose of M16αα is based on safety and PK considerations in a previous, single-dose study in healthy volunteers and preclinical data.

Placebo: 130 mg micro crystalline cellulose in gelatin capsule.

Administration: oral, before breakfast, with 240 ml water, for both drug and placebo. M16αα or placebo were administered orally for 28 consecutive days, followed by additional 28 days of placebo. End of Study (EOS) visit took place about 4 weeks after last dose of M16αα administered.

During this period, safety, PD and $C_{ss}$ assessments were performed by the WMC and DMC Diabetes Clinics.

The subjects underwent CGMS and oral glucose tolerance test prior to, during treatment, and on End of Study (EOS) visit.

Safety

Intra subject physical parameters did not change over the course of the study. Clinical pathology, hematology, urinalysis and ECG parameters were within the normal range or within ranges considered to be characteristic for uncontrolled T2D patients. A total of 20 AE were reported. 7 AE occurred in subjects that were administered the add-on placebo. AE were single events, mild in intensity and intermittent in frequency. No serious adverse events (SAE) were recorded. Taken collectively, M16αα treatment was well tolerated and safe for the duration of study dosing.

Efficacy:

Efficacy was evaluated by effects of M16αα on glycemic control [(HbA1c); fasting blood glucose (FBG); sum of plasma glucose values during OGTT (0, 30, 60, 120, 180) (Eglucose); % of time with measured glucose levels lower than 180 mg % during continuous glucose monitoring (CGM) (CGM(<180 mg %)]; Sensitization to insulin [Hepatic insulin sensitization index (HepISI); Composite insulin sensitization index (CompISI); HOMA insulin resistance (HOMAIR)]; beta-cell rest [HOMA % B; sum of plasma c-peptide values during OGTT (0, 30, 60, 120, 180) (Ecpeptide)], and non-glycemic aspects [plasma triglycerides (TRIG); body weight].

Note: due to M16αα delayed pharmacokinetics as compared with the relatively short M16αα dosing period of 28 d, changes in efficacy parameters are presented below irrespective of whether attained at the end of the drug dosing period or at the end of the recovery period. Weighted average changes in baseline efficacy parameters are presented below for all patients medicated with add-on M16αα, independently of their anti-diabetic medication history (as shown in Table 1 below).

Sample results are presented in Table 1 below. Overall results and significance are summarized in Table 2 below.

TABLE 1

| | Patient | Ongoing anti-diabetic treatment | | HbA1c Day 28 | HbA1c Day 90 - extrapolated* | HP ISI | Comp ISI | IR |
|---|---|---|---|---|---|---|---|---|
| Cohort 1 | 101 | + | before | 7.4 | 7.4 | 0.8 | 4.9 | 1.4 |
| | | | after | 6.9 | 5.9 | 2.3 | 5.0 | 0.6 |
| | 102 | + | before | 7.5 | 7.5 | 1.0 | 5.5 | 0.8 |
| | | | after | 6.8 | 5.4 | 2.1 | 10.10 | 0.5 |
| | 106 | + | before | 7.4 | 7.4 | 1.8 | 12.1 | 0.65 |
| | | | after | 6.7 | 5.3 | 9.5 | 19.17 | 0.4 |
| | 108 | none | before | 7.5 | 7.5 | 0.7 | 4.4 | 1.4 |
| | | | after | 7.6 | 7.6 | 1.6 | 5.8 | 0.6 |
| Cohort 2 | 202 | + | before | 7.2 | 7.2 | 0.2 | 3.3 | 4.0 |
| | | | after | 6.8 | 6.0 | 0.4 | 2.2 | 2.2 |
| | 205 | + | before | 8.0 | 8.0 | 0.5 | 2.9 | 2.3 |
| | | | after | 8.1 | 8.1 | 0.6 | 4.7 | 1.8 |
| | 206 | + | before | 8.6 | 8.6 | 0.6 | 3.2 | 1.4 |
| | | | after | 7.1 | 4.1 | 1.1 | 5.5 | 0.9 |
| Placebo | 208 | + | before | 9.4 | 9.4 | 0.2 | 1.4 | 3.8 |
| | | | after | 10.3 | 10.3 | 0.1 | 1.3 | 5.4 |
| Cohort 3 | 301 | + | before | 8.21 | | 0.71 | 4.6 | 1.4 |
| | | | after | 8.17 | | 0.79 | | 1.4 |
| | 302 | + | before | 7.80 | | 1.01 | 5.7 | 1.3 |
| | | | after | 7.33 | | 0.88 | 4.6 | 1.1 |
| | 303 | + | before | 7.67 | | 1.44 | 6.7 | 0.8 |
| | | | after | 7.52 | | 1.33 | 6.9 | 0.8 |
| | 304 | | before | 8.84 | | 0.7 | 3.1 | 1.25 |
| | | | after | 8.73 | | 1.41 | 6.3 | 0.7 |

*Extrapolated from values obtained, considering linear progressive glycosylation of HbA1C by blood glucose throughout 90 days of the erythrocytes survival in blood, see description above

TABLE 2

| Efficacy parameter | Baseline | Change in Baseline | Significance* |
|---|---|---|---|
| Glycemic control | | | |
| HbA1C (%) (28 d) | 7.96 ± 0.81 | Decrease by 0.48 (5.28 mmol/mol) (eAG 14 mg/dL) | 0.00015 |
| HbA1C (%) (Estimated 90 d)[1,2] | — | Decrease by 0.96-1.44 (10.6-15.8 mmol/mol) (eAG 28-42 mg/dL) | — |
| Fasting blood glucose (FBG) | 159 ± 56 mg/dL | Decrease by 11.7% | 0.0009 |
| Σglucose (OGTT 0, 30, 60, 120, 180 min) | 100 | Decrease by 7.8% | 0.0075 |
| Continuous glucose monitoring [CGM(<180 mg %)] | 71 ± 25% | Increase by 8.4% | 0.2760 |
| Sensitization to insulin | | | |
| Hepatic insulin sensitization index [(HepISI] | 1.0 | Increase by 2.50-fold | 0.0001 |
| Composite insulin sensitization index (CompISI) | 1.0 | Increase by 2.04-fold | 0.0009 |
| HOMA insulin resistance (HOMAIR) | 1.0 | Increase by 0.59-fold | 0.0001 |
| Beta-cell Rest | | | |
| HOMA % B | 1.0 | Decrease by 0.81-fold | 0.0188 |
| Σc-peptide (OGTT 0, 30, 60, 120, 180 min) | 100 | Decrease by 17% | 0.0287 |
| Non-glycemic aspects | | | |
| Plasma triglycerides | 169 ± 95 mg/dL | Decrease by 18% | 0.0001 |
| Bodyweight | 88 ± 9 kg | Decrease by 0.6 kg | 0.0740 |
| Hypertension | 136 ± 13/75 ± 7 | Decrease in 5 patients | — |

*Differences between baseline (V1, 2, 3) and end of treatment (V7 and/or V9) for each efficacy parameter were analyzed using the Wilkcoxon matched-pairs signed-ranks test. 1-tailed p-values.
[1]Hirst J A, et al., ibid.
[2]Beltran Del Rio M, ibid.

Summary of M16αα Competitive Edge:

a. The prospective glucose-lowering activity of add-on M16αα surpasses those reported for current SoC oral antidiabetic drugs.

b. Metformin and pioglitazone (Pio) are the only antidiabetic drugs reported to induce sensitization to insulin, while sulphonylurea, meglitinides, DPP4i, GLP1 analogs and SGLT2i are all devoid of an insulin-sensitizing activity. The insulin sensitizing activity of M16αα added-on to metformin surpasses that reported for add-on Pio.

c. Beta-cell rest by M16αα, combined with its robust insulin-sensitizing activity may predict efficacy in maintaining long-term beta-cell function in T2D patients.

d. The insulin-sensitizing activity of M16αα combined with its activity in lowering plasma insulin may predict alleviation of the non-glycemic diseases of T2D.

e. M16αα may offer an All-in-One treatment mode for T2D patients, thus avoiding the higher risk of adverse reactions, complicated treatment protocols and high cost of the multiple drug approach to T2D.

f. M16αα may offer a First-in-Line drug for treating the Metabolic Syndrome.

The invention claimed is:

1. A method of at least one of:
(a) treating type 2 diabetes mellitus in a human subject in need thereof;
(b) treating and/or preventing a pathology, symptom and/or disease that is an adverse effect of type 2 diabetes mellitus in a human subject in need thereof;
(c) preventing and/or delaying the onset of type 2 diabetes mellitus or the onset of anti-diabetic treatment in a pre-type 2 diabetic human subject, or in an impaired-glucose tolerance (IGT) human subject, or in an impaired fasting glucose (IFG) human subject;
(d) decreasing insulin resistance, and/or fasting blood glucose level, and/or level of glycosylated hemoglobin A1C, and/or increasing glucose tolerance in insulin-resistant pre-type 2 diabetic or hyperglycemic type 2 diabetes mellitus human subject; and
(e) maintaining or reducing standard-of-care administered dose of an anti-diabetic drug or for obviating the need for administration of such drug in a human type 2 diabetes mellitus subject,
wherein said human subject is receiving ongoing standard-of-care antidiabetic treatment comprising (1) Therapeutic Lifestyle Change (TLC) including dietary measures and/or physical exercise and/or (2) administration of at least one anti-diabetic drug,
said method comprising administering to said human subject a therapeutically effective amount of an amphipathic α,α-substituted long-chain dicarboxylic acid of the formula (I):

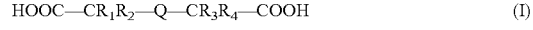

$$HOOC-CR_1R_2-Q-CR_3R_4-COOH \quad (I)$$

wherein
$R_1$, $R_2$, $R_3$ and $R_4$, each independently represents a lower alkyl or a lower alkoxy group; and
Q represents a diradical consisting of a linear chain of 12 to 16 carbon atoms,
or a pharmaceutically acceptable salt, ester, or anhydride thereof.

2. The method of claim 1, wherein said α,α-substituted long-chain dicarboxylic acid or pharmaceutically acceptable salt, esteror anhydride thereof is administered orally.

3. The method of claim 1, wherein said ongoing standard-of-care treatment comprises orally administering to said patient an anti-diabetic drug that is any one of metformin, a sulphonylurea, a DPP4 inhibitor or a SGLT2 inhibitor, and/or parenterally administering to said patient an anti-diabetic drug that is any one of a Glucagon-like-Peptide 1 (GLP-1) analog, insulin or an insulin analog.

4. The method of claim 1, wherein said pathology, symptom and/or disease that is an adverse effect of type 2 diabetes mellitus is any one of insulin resistance, hyperglycemia, obesity/overweight, diabetic dyslipidemia, diabetic hypertriglyceridemia, diabetes-associated neurodegeneration, diabetes macrovascular disease, or diabetes microvascular disease.

5. The method of claim 1, wherein said therapeutically effective amount of said α,α-substituted long-chain dicarboxylic acid or pharmaceutically acceptable salt, ester, or anhydride thereof administered to said human subject is from about 10 mg per day to about 200 mg per day, 10 mg per day to about 150 mg per day, 10 mg per day to about 100 mg per day, or 10 mg per day to about 50 mg per day, administered to said subject once or twice daily, or once, twice or three times weekly, and/or administered chronically.

6. The method of claim 1, wherein insulin resistance of said subject is decreased compared to the insulin resistance of said subject before/without treatment with said amphipathic α,α-substituted long-chain dicarboxylic acid or pharmaceutically acceptable salt, ester or anhydride thereof; and/or the level of fasting plasma/blood glucose of said subject is decreased compared to the fasting plasma/blood glucose of said subject before/without treatment with said amphipathic α,α-substituted long-chain dicarboxylic acid or pharmaceutically acceptable salt, ester or anhydride thereof; and/or the blood level of glycosylated hemoglobin $A1_C$ of said subject is decreased compared to the level of glycosylated hemoglobin $A1_C$ of said subject before/without treatment with said amphipathic α,α-substituted long-chain dicarboxylic acid or pharmaceutically acceptable salt, ester or anhydride thereof; and/or glucose tolerance of said subject is increased compared to the glucose tolerance of said subject before/without treatment with said amphipathic α,α-substituted long-chain dicarboxylic acid or pharmaceutically acceptable salt, ester or anhydride thereof.

7. The method of claim 1, wherein said dicarboxylic acid is a dicarboxylic acid of the formula HOOC—C(CH$_3$)$_2$—(CH)$_n$—C(CH$_3$)$_2$—COOH, wherein n is an integer of from 12 to 16.

8. The method of claim 1, wherein said dicarboxylic acid is:
- 2,2,15,15-tetramethylhexadecane-1,16-dioic acid (also referred to herein as M16αα);
- 2,2,17,17-tetramethyloctadecane-1,18-dioic acid (also referred to herein as M18αα); or
- 2,2,19,19-tetramethyloctadecane-1,20-dioic acid (also referred to herein as M20αα).

9. A method for at least one of:
(a) treating type 2 diabetes mellitus in a human subject in need thereof;
(b) treating and/or preventing a pathology, symptom and/or disease that is an adverse effect of type 2 diabetes mellitus in a human subject in need thereof;
(c) preventing and/or delaying the onset of type 2 diabetes mellitus or the onset of anti-diabetic treatment in a pre-type 2 diabetic subject, or in an impaired-glucose tolerance (IGT) subject, or in an impaired fasting glucose (IFG) subject; and
(d) decreasing insulin resistance, and/or fasting plasma glucose level, and/or blood level of glycosylated hemoglobin A1C, and/or increasing glucose tolerance in pre-type 2 diabetic or hyperglycemic type 2 diabetes mellitus human subject,
said method comprising administering to said human subject a therapeutically effective amount of an amphipathic α,α-substituted long-chain dicarboxylic acid of the formula (I):

HOOC—CR$_1$R$_2$—Q—CR$_3$R$_4$—COOH     (I)

wherein
R$_1$, R$_2$, R$_3$ and R$_4$, each independently represents an a lower alkyl or a lower alkoxy group; and
Q represents a diradical consisting of a linear chain of 12 to 16 carbon atoms,
or a pharmaceutically acceptable salt, ester, or anhydride thereof, wherein said therapeutically effective amount of said amphipathic α,α-substituted long-chain dicarboxylic acid or pharmaceutically acceptable salt, ester or anhydride thereof is in an amount of from about 10 mg per day to about 45 mg per day, with the proviso that said human subject is one not already being treated with antidiabetic standard-of-care treatment.

10. The method of claim 9, wherein said pathology, symptom or disease that is an adverse effect of type 2 diabetes mellitus is any one of insulin resistance, hyperglycemia, obesity/overweight, diabetic dyslipidemia, diabetic hyper-triglyceridemia, diabetes-associated neurodegeneration, diabetes macrovascular disease, or diabetes microvascular disease.

11. The method of claim 9, wherein insulin resistance of said subject is decreased compared to the insulin resistance of said subject before/without treatment with said amphipathic α,α-substituted long-chain dicarboxylic acid or pharmaceutically acceptable salt, ester or anhydride thereof; and/or the level of fasting plasma/blood glucose of said subject is decreased compared to the fasting plasma/blood glucose of said subject before/without treatment with said amphipathic α,α-substituted long-chain dicarboxylic acid or pharmaceutically acceptable salt, ester or anhydride thereof; and/or the plasma level of glycosylated hemoglobin $A1_C$ of said subject is decreased compared to the plasma level of glycosylated hemoglobin $A1_C$ of said subject before/without treatment with said amphipathic α,α-substituted long-chain dicarboxylic acid or pharmaceutically acceptable salt, ester or anhydride thereof; and/or glucose tolerance of said subject is improved compared to the glucose tolerance of said subject before/without treatment with said amphipathic α,α-substituted long-chain dicarboxylic acid or pharmaceutically acceptable salt, ester or anhydride thereof.

12. The method of claim 9, wherein said α,α-substituted long-chain dicarboxylic acid or pharmaceutically acceptable salt, esteror anhydride thereof is administered orally.

13. The method of claim 9, wherein said amphipathic α,α-substituted long-chain dicarboxylic acid or pharmaceutically acceptable salt, ester ester or anhydride thereof is administered at a dose of from about 10 mg per day to about 200 mg per day, 10 mg per day to about 150 mg per day, 10 mg per day to about 100 mg per day, or 10 mg per day to about 50 mg per day.

14. The method of claim 9, wherein said amphipathic α,α-substituted long-chain dicarboxylic acid or pharmaceutically acceptable salt, ester or anhydride thereof is administered once or twice daily, or is administered once, twice or three times weekly and/or is administered chronically.

15. The method of claim 9, wherein said dicarboxylic acid is a dicarboxylic acid of the formula HOOC—C(CH$_3$)$_2$—(CH)$_n$—C(CH$_3$)$_2$—COOH, wherein n is an integer of from 12 to 16.

16. The method of claim 9, wherein said dicarboxylic acid is:
(a) 2,2,15,15-tetramethylhexadecane-1,16-dioic acid (also referred to herein as M16αα);
(b) 2,2,17,17-tetramethyloctadecane-1,18-dioic acid (also referred to herein as M18αα); or
(c) 2,2,19,19-tetramethyloctadecane-1,20-dioic acid (also referred to herein as M20αα).

* * * * *